US010905628B2

(12) United States Patent
Hodges, IV

(10) Patent No.: US 10,905,628 B2
(45) Date of Patent: Feb. 2, 2021

(54) SYSTEMS AND METHODS FOR THERAPEUTIC STIMULATION VIA GARMENTS AND INSERTS PROVIDED THEREON

(71) Applicant: Charles Edward Hodges, IV, Libertyville, IL (US)

(72) Inventor: Charles Edward Hodges, IV, Libertyville, IL (US)

(73) Assignee: THERAPEUTIC ENVISIONS, INC., Libertyville, IL (US)

( * ) Notice: Subject to any disclaimer, the term of this patent is extended or adjusted under 35 U.S.C. 154(b) by 1126 days.

(21) Appl. No.: 15/167,548

(22) Filed: May 27, 2016

(65) Prior Publication Data
US 2016/0346153 A1    Dec. 1, 2016

Related U.S. Application Data

(60) Provisional application No. 62/166,987, filed on May 27, 2015.

(51) Int. Cl.
*A61H 1/00*        (2006.01)
*A61H 23/02*       (2006.01)
(Continued)

(52) U.S. Cl.
CPC .......... *A61H 23/02* (2013.01); *A61B 5/0024* (2013.01); *A61B 5/6804* (2013.01); *A61F 7/02* (2013.01);
(Continued)

(58) Field of Classification Search
CPC ............ A61H 23/02; A61H 2201/5028; A61H 2205/108; A61H 2205/106;
(Continued)

(56) References Cited

U.S. PATENT DOCUMENTS 2,792,830 A * 5/1957 Dacey .................... A61H 23/02
601/18
3,710,784 A * 1/1973 Taylor ................ A61H 23/0263
601/18

(Continued)

*Primary Examiner* — Quang D Thanh
(74) *Attorney, Agent, or Firm* — Kilpatrick Townsend & Stockton LLP

(57) ABSTRACT

According to the invention, a system for applying therapeutic stimulation to a human body may include a garment and a therapeutic insert. The garment may include a flexible material configured to apply compressive forces to a portion of a person wearing the garment, a communication interface, and an attachment point. The therapeutic insert may include a vibration unit configured to vibrate against the person, and to activate upon an instruction being received from the communication interface. The therapeutic insert may also include a thermal unit configured to apply heating or cooling to the person, and to activate upon an instruction being received from the communication interface. The therapeutic insert may further include a sensor configured to determine a physiological characteristic of the person, and to communicate the physiological characteristic to the communication interface. The therapeutic insert may be configured to couple with the attachment point.

16 Claims, 3 Drawing Sheets

(51) Int. Cl.

| | | |
|---|---|---|
| *A61F 7/08* | (2006.01) | |
| *G06F 19/00* | (2018.01) | |
| *A61B 5/00* | (2006.01) | |
| *G16H 40/63* | (2018.01) | |
| *A61F 7/02* | (2006.01) | |
| *A61F 7/00* | (2006.01) | |

(52) U.S. Cl.
CPC ......... *G06F 19/3481* (2013.01); *G16H 40/63* (2018.01); *A61F 2007/0039* (2013.01); *A61F 2007/0086* (2013.01); *A61F 2007/0093* (2013.01); *A61F 2007/0096* (2013.01); *A61F 2007/0233* (2013.01); *A61H 2201/0207* (2013.01); *A61H 2201/0214* (2013.01); *A61H 2201/0228* (2013.01); *A61H 2201/1207* (2013.01); *A61H 2201/164* (2013.01); *A61H 2201/165* (2013.01); *A61H 2201/169* (2013.01); *A61H 2201/1645* (2013.01); *A61H 2201/5012* (2013.01); *A61H 2201/5015* (2013.01); *A61H 2201/5028* (2013.01); *A61H 2201/5097* (2013.01); *A61H 2205/06* (2013.01); *A61H 2205/10* (2013.01); *A61H 2205/106* (2013.01); *A61H 2205/108* (2013.01); *G08C 2201/93* (2013.01)

(58) Field of Classification Search
CPC ............ A61H 2205/10; A61H 2205/06; A61H 2201/5015; A61H 2201/5012; A61H 2201/169; A61H 2201/16; A61H 2201/1645; A61H 2201/164; A61H 2201/1207; A61H 2201/0228; A61H 2201/5097; A61H 2201/0207; A61H 2201/0214; A61F 7/02; A61F 2007/0233; A61F 2007/0096; A61F 2007/0086; A61F 2007/0039; A61F 2007/0093; G16H 40/63; A61B 5/6804; A61B 5/0024; G06F 19/3481; G08C 2201/93
See application file for complete search history.

(56) References Cited

U.S. PATENT DOCUMENTS

| | | | | |
|---|---|---|---|---|
| 4,979,502 | A  * | 12/1990 | Hunt | ...... A61H 23/02 |
| | | | | 601/15 |
| 6,193,678 | B1 * | 2/2001 | Brannon | ........... A61H 23/0263 |
| | | | | 601/15 |
| 6,329,638 | B1 * | 12/2001 | Bloodworth | ........... A61H 23/02 |
| | | | | 219/211 |
| 7,207,953 | B1 * | 4/2007 | Goicaj | ................... A61H 23/02 |
| | | | | 601/134 |
| 2004/0133133 | A1* | 7/2004 | Dreimann | ......... A61H 23/0263 |
| | | | | 601/15 |
| 2004/0260211 | A1* | 12/2004 | Maalouf | ................ A61H 23/02 |
| | | | | 601/15 |
| 2006/0258962 | A1* | 11/2006 | Kopanic | ................... A61F 7/03 |
| | | | | 601/15 |
| 2007/0255187 | A1* | 11/2007 | Branch | ..................... A61F 7/02 |
| | | | | 601/15 |
| 2016/0128632 | A1* | 5/2016 | Wiebe | ................. A61B 5/0015 |
| | | | | 340/870.07 |
| 2016/0324487 | A1* | 11/2016 | Guo | .................. G08B 21/0269 |
| 2018/0093121 | A1* | 4/2018 | Matsuura | ............... G09B 23/28 |

\* cited by examiner

SYSTEMS AND METHODS FOR THERAPEUTIC STIMULATION VIA GARMENTS AND INSERTS PROVIDED THEREON

CROSS-REFERENCE TO RELATED APPLICATIONS

This application claims priority to Provisional U.S. Patent Application No. 62/166,987 filed May 27, 2015, entitled "SYSTEMS AND METHODS FOR THERAPEUTIC EXTERNAL STIMULI AND CONTRAST THERAPY APPLICATIONS TO THE HUMAN BODY," the entire disclosure of which is hereby incorporated by reference, for all purposes, as if fully set forth herein.

BRIEF DESCRIPTION OF THE INVENTION

In one embodiment, a system for applying therapeutic stimulation to a human body is provided. The system may include a garment and a therapeutic insert. The garment may include a flexible material configured to apply compressive forces to a portion of a person wearing the garment, a communication interface, and an attachment point. The therapeutic insert may include a vibration unit configured to vibrate against the person, and to activate upon an instruction being received from the communication interface. The therapeutic insert may also include a thermal unit configured to apply heating or cooling to the person, and to activate upon an instruction being received from the communication interface. The therapeutic insert may further include a sensor configured to determine a physiological characteristic of the person, and to communicate the physiological characteristic to the communication interface. The therapeutic insert may be configured to couple with the attachment point.

In another embodiment, a system for applying therapeutic stimulation to a human body is provided. The system may include a garment and a therapeutic insert. The garment may include a flexible material configured to apply compressive forces to a portion of a person wearing the garment, a communication interface, and an attachment point. The garment may also include a thermal element configured to apply heating or cooling to the person. The therapeutic insert may include a vibration unit configured to vibrate against the person, and to activate upon an instruction being received from the communication interface. The therapeutic insert may also include a sensor configured to determine a physiological characteristic of the person. The therapeutic insert may be configured to couple with the attachment point.

In another embodiment, a system for applying therapeutic stimulation to a human body is provided. The system may include a garment and a therapeutic insert. The garment may include a flexible material configured to apply compressive forces to a portion of a person wearing the garment, a communication interface, and two attachment points. The therapeutic insert may be a flexible lengthwise member and a vibration unit along at least a portion of the length of the lengthwise member configured to vibrate against the person, and to activate upon an instruction being received from the communication interface. The first therapeutic insert may be configured to couple with the attachment points at at least each end of the lengthwise member.

BRIEF DESCRIPTION OF THE DRAWINGS

The present invention is described in conjunction with the appended figures.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

For example, any detail discussed with regard to one embodiment may or may not be present in all contemplated versions of that embodiment. Likewise, any detail discussed with regard to one embodiment may or may not be present in all contemplated versions of other embodiments discussed herein. Finally, the absence of discussion of any detail with regard to embodiment herein shall be an implicit recognition that such detail may or may not be present in any version of any embodiment discussed herein (i.e., that negative claim limitations are supported for any matter not discussed explicitly herein).

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Figure 1:
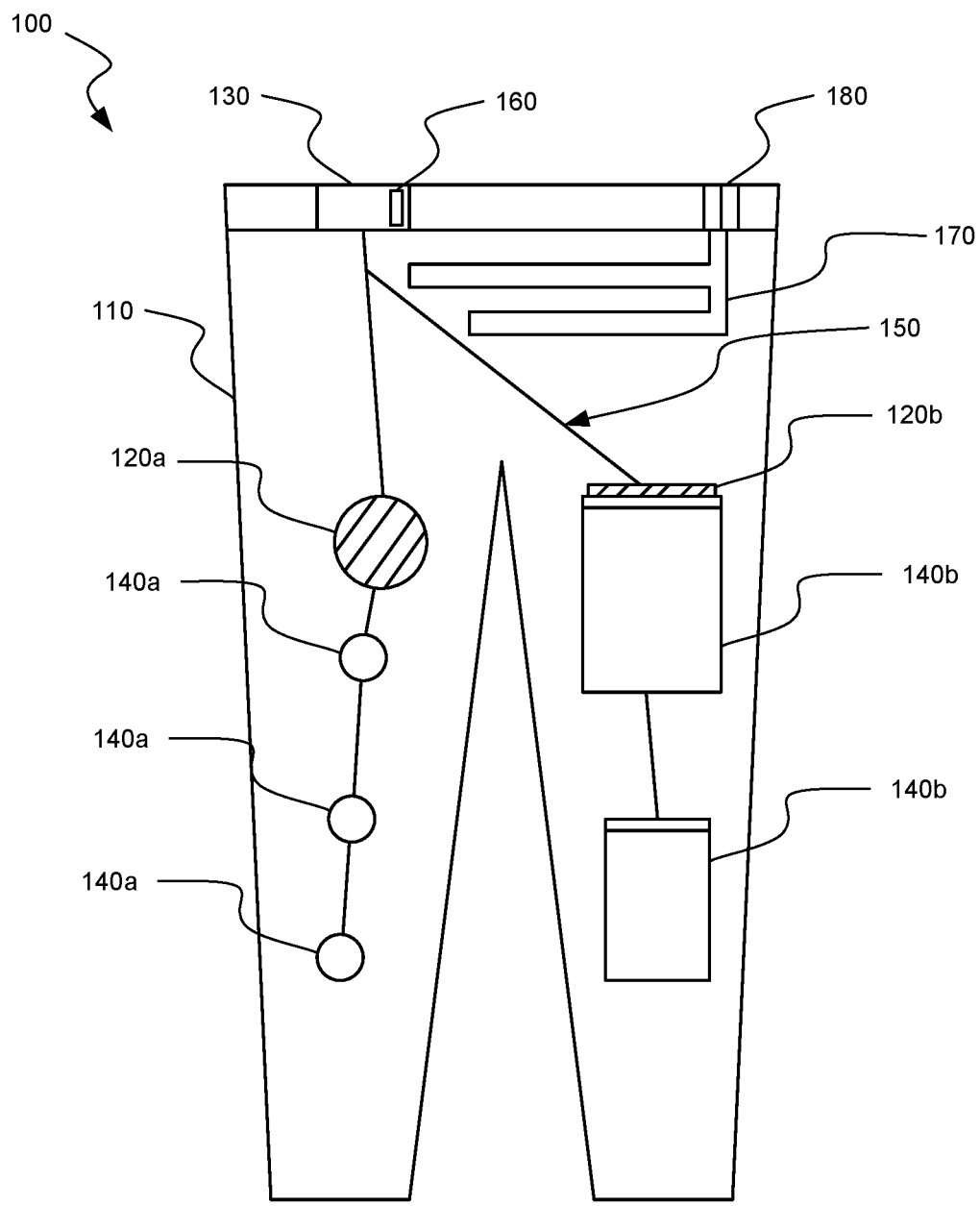
FIG. 1 is an schematic view of one embodiment of the invention for applying therapeutic stimulation to a human body via a garment with at least one therapeutic insert disposed thereon.

Turning now to FIG. 1, one system 100 of the invention is shown. System 100 may be for applying therapeutic stimulation to a human body via a garment 110 with at least one therapeutic insert 120 disposed thereon.

In the embodiment shown, garment 110 is a pair of pants, but in other embodiments may be other articles of clothing or any other arrangement of material which covers a portion of a human body. For example, pants, bodysuits, arm sleeves, leg sleeves, etc. Garment 110 may be made from a flexible material configured to apply compressive forces to a portion of a person wearing the garment.

Garment 110 may also include a communication interface 130 and one or more attachment points 140 where therapeutic inserts may be disposed or coupled thereon. Communication interface 130 may be coupled with attachment points 140 via a communication line 150. Communication interface 130 may be a hardline interface (for example, USB, and the like), or may be a wireless interface (for example, WiFi, Bluetooth, and the like). In some embodiments, communication interface 130 may also include tactile activated controls thereon capable of performing any action described herein.

Attachment points 140 may provide a manner for electronically coupling with therapeutic inserts 120. Attachment points 140 may be constructed in numerous possible manners. In this example, attachment points 140a may be hook and loop, button, or other mechanical connectors of the like. Other types of attachment points 140 may be possible, such as attachments points 140b which are shown as pockets. While in this embodiment different types of attachment points 140 are shown on the same garment, in some embodiments all attachment points 140 will be of the same, or even more varied type, depending on the application and geography of the relevant body portion as well as the shape and the size of an intended therapeutic insert 120 intended for the location. Any number of attachment points 140 may be present in any number of locations depending on the embodiment.

Figure 2:
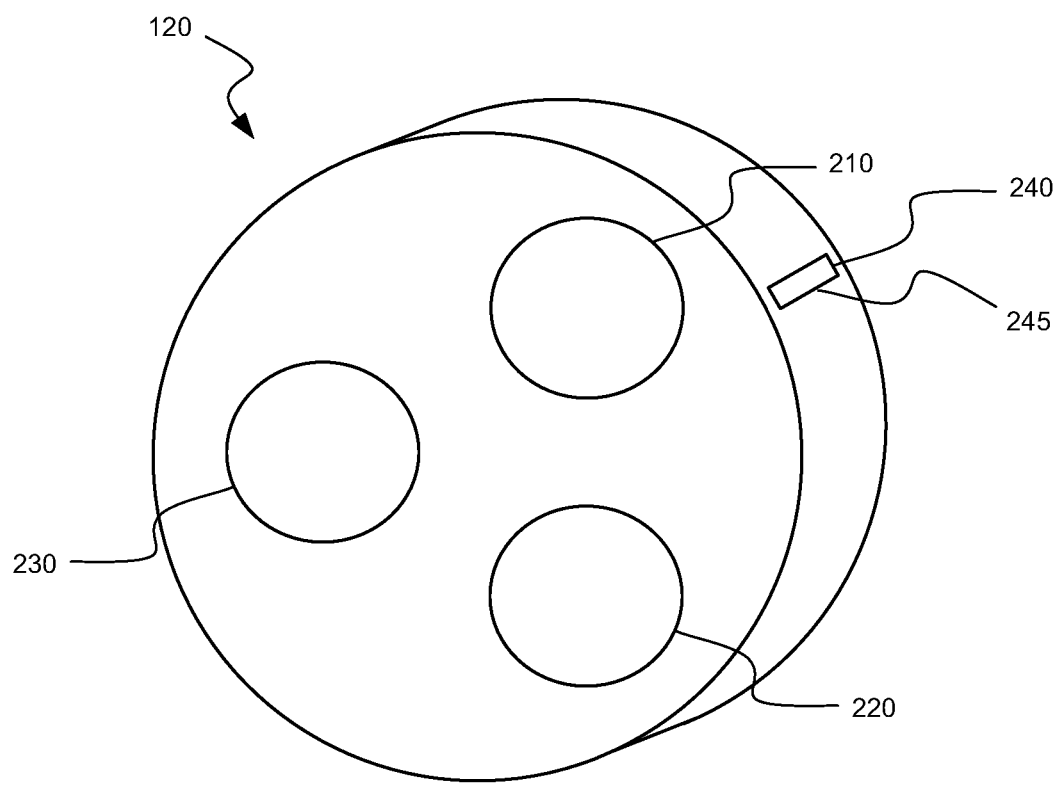
FIG. 2 is a schematic view of an one possible therapeutic insert of the invention.

Therapeutic inserts 120, shown in greater detail in FIG. 2 may include a vibration unit 210 configured to vibrate against the person, and to activate upon a first instruction being received from communication interface 130. Alternatively, vibration unit 210 may activate upon a signal received directly by therapeutic insert 120, without communication interface 130 being involved. While therapeutic insert 120 is shown in this embodiment as round (matching therapeutic insert 120a from FIG. 1), therapeutic inserts 120 may also be provided in other shapes, for example rectangular as shown by therapeutic insert 120b from FIG. 1).

Therapeutic insert 120 may also include a thermal unit 220 configured to apply heating or cooling to the person, and possibly to activate upon a second instruction being received from the communication interface. Alternatively, thermal unit 220 may activate upon a signal received directly by therapeutic insert 120, without communication interface 130 being involved. In another alternative embodiment, thermal unit 220 may be passive, in that it is pre-heated or pre-cooled prior to being coupled with garment 110.

Therapeutic insert 120 may also include a sensor 230 configured to determine a physiological characteristic of the person (for example, heart rate, temperature, pulse, etc.), and possibly to activate or report upon a third instruction being received from the communication interface. Alternatively, sensor 230 may activate or report upon a signal received directly by therapeutic insert 120, without communication interface 130 being involved. In some embodiments, vibration unit 210, thermal unit 220, and sensor 230 may not all be present in any given therapeutic insert 120.

In any of the above described or other embodiments, a single instruction may also activate or cause an action to be taken by any combination of vibration unit 210, thermal unit 220, and/or sensor 230. Single or multiple instructions may also control a given addressable therapeutic insert 120 or any addressable subcomponent thereof. These instructions may be initiated by controls at communication interface 130 or at some device such as a computer, tablet, mobile device, etc. which is in communication with communication interface 130. In some embodiments, applications running on such devices may receive data back from, and control, therapeutic inserts 120. The application or device used to submit instructions to communication interface 130 and/or therapeutic inserts 120 may allow for a user or clinician to provide a predetermined sequence and/or pattern of operation for a set number, or variable number of therapeutic inserts 120 present in a given embodiments. Any sub portion of any therapeutic insert 120 may be controlled by such sequence/pattern. In one example, therapeutic inserts may be controlled to correspond their activation with a music or other source on the mobile device.

Therapeutic insert 120 may also include a charging port 240. In some embodiments, charging port 240 may also be a point at which attachment point 140 interfaces with therapeutic insert 120. In some embodiments, charging port 240 may be the sole point at which attachment point 140 interfaces with therapeutic insert 120. Thus, charging port 240 may also be a communication port 245 for therapeutic insert 120. A charging port 160 may also be present on garment 110 to provide power via communication line 150.

In some embodiments, alternative or in addition to thermal units 220, garment 110 may also include a thermal element 170 which allows for thermal transfer with the person wearing garment 110 without use of thermal units 220. Thermal ports 180 may provide for an electrical, fluid, or other connection in order to provide or remove energy from thermal element 170. Thermal ports 180 may be located at any position on garment 110. Likewise, thermal element 170 may cover any portion or entirety of garment 110.

Figure 3:
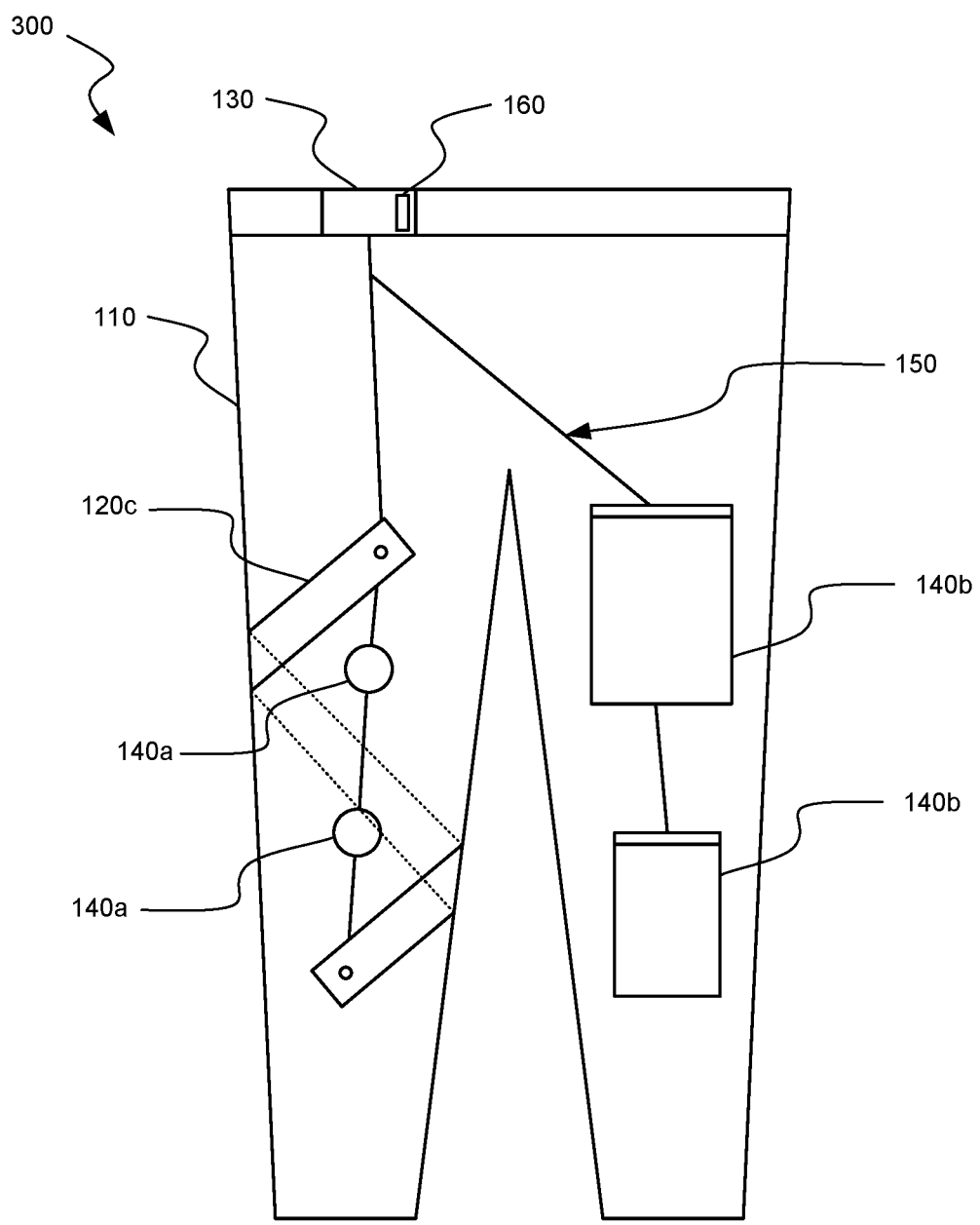
FIG. 3 is a schematic view of another embodiment of the invention for applying therapeutic stimulation to a human body via a garment with a different therapeutic insert disposed thereon.

FIG. 3 shows another embodiment 300 of the invention similar to that of FIG. 1, but with a different therapeutic insert 120c shown. In this embodiment, therapeutic insert 120c includes a flexible lengthwise strap-like element which couples with two attachment points 140. Therapeutic insert 120c is shown in this example as wrapping around the leg of garment 110. In other embodiment, different configurations of therapeutic insert 120c may be provided. For example, therapeutic insert 120c could wrap around different portions of the body in different manners, and also have different lengths and widths. Also, an attachment to zero, one, two, three, or more attachment points could be used by therapeutic insert 120c in different embodiments. Therapeutic insert 120c may have vibration units, thermal units, and/or sensors therein, just as other therapeutic inserts 120 described herein. A vibration unit in such a strap may include a electromechanically vibrating disc at either end of the strap, with a coil within the strap conducting movement across the length of the strap.

In some embodiments, therapeutic inserts 120 may communicate or otherwise interact with each other. Merely by way of example, one therapeutic insert 120 may pass along instructions to other therapeutic inserts so that all or any sub-portion of all therapeutic inserts 120 may work sequentially or in parallel in an ordered manner.

In other embodiments, signals such as audible, optical, magnetic, or radio-wave signals may be transmitted by one therapeutic insert 120 to another therapeutic insert 120. Any change in the transmitted signal to the received signal, or a change in two received signals over time, may be indicative of a change in state of a body part between such two therapeutic inserts 120. For example, wear, fatigue, or injury may be recognized by an algorithm examining data returned from therapeutic inserts 120.

The invention has now been described in detail for the purposes of clarity and understanding. However, it will be appreciated that certain changes and modifications may be practiced within the scope of the appended claims.

What is claimed is:

1. A system for applying therapeutic stimulation to a human body via a garment with at least one insert disposed thereon, wherein the system comprises:
a garment, wherein the garment comprises:
a flexible material configured to apply compressive forces to a portion of a person wearing the garment;
a thermal element that is integrated into the garment and coupled with at least a portion of the flexible material;
a thermal port that is integrated into the garment that provides a fluid connection that is configured to provide or remove energy from the thermal element;
a communication interface; and
a first attachment point in a first location; and
a first therapeutic insert, wherein:
the first therapeutic insert comprises:
a vibration unit configured to vibrate against the person, and to activate upon a first instruction being received from the communication interface;
a thermal unit configured to apply heating or cooling to the person, and to activate upon a second instruction being received from the communication interface; and
a sensor configured to determine a physiological characteristic of the person, and to communicate the physiological characteristic to the communication interface; and
the first therapeutic insert is configured to couple with the first attachment point.

2. The system for applying therapeutic stimulation to the human body via the garment with the at least one insert disposed thereon of claim 1, wherein the first therapeutic insert comprises:
a charging port configured to provide power to the first therapeutic insert.

3. The system for applying therapeutic stimulation to the human body via the garment with the at least one insert disposed thereon of claim 1, wherein the first instruction and the second instruction are:
a single instruction.

4. The system for applying therapeutic stimulation to the human body via the garment with the at least one insert disposed thereon of claim 1, wherein the first attachment point comprises:
a pocket.

5. The system for applying therapeutic stimulation to the human body via the garment with the at least one insert disposed thereon of claim 1, wherein the first attachment point comprises:
a hook and loop fastening feature.

6. The system for applying therapeutic stimulation to the human body via the garment with the at least one insert disposed thereon of claim 1, wherein the communication interface comprises:
a wireless communication device.

7. The system for applying therapeutic stimulation to the human body via the garment with the at least one insert disposed thereon of claim 1, wherein the first therapeutic insert further comprises:
a first communication port.

8. The system for applying therapeutic stimulation to the human body via the garment with the at least one insert disposed thereon of claim 7, wherein the garment further comprises:

a communication line coupling a charging port of the garment with the first therapeutic insert.

9. The system for applying therapeutic stimulation to the human body via the garment with the at least one insert disposed thereon of claim 8, wherein the garment further comprises:
a charging and communications port that is integrated into the garment, is coupled with the flexible material, and is coupled with the communication line and configured to provide power to the first therapeutic insert.

10. The system for applying therapeutic stimulation to the human body via the garment with the at least one insert disposed thereon of claim 1, wherein:
the garment further comprises a second attachment point in a second location; and
the system further comprises a second therapeutic insert, wherein:
the second therapeutic insert comprises:
a vibration unit configured to vibrate against the person, and to activate upon a third instruction being received from the communication interface;
a thermal unit configured to apply heating or cooling to the person, and to activate upon a fourth instruction being received from the communication interface; and
a sensor configured to determine a physiological characteristic of the person, and to communicate the physiological characteristic to the communication interface; and
the second therapeutic insert is configured to couple with the second attachment point.

11. The system for applying therapeutic stimulation to the human body via the garment with the at least one insert disposed thereon of claim 10, wherein the first instruction and the third instruction are:
a single instruction.

12. The system for applying therapeutic stimulation to the human body via the garment with the with at least one insert disposed thereon of claim 10, wherein the second instruction and the fourth instruction are:
a single instruction.

13. The system for applying therapeutic stimulation to the human body via the garment with the at least one insert disposed thereon of claim 10, wherein the first instruction, second instruction, third instruction, and fourth instruction are:
a single instruction.

14. The system for applying therapeutic stimulation to the human body via the garment with the at least one insert disposed thereon of claim 1, wherein:
the communications interface is integrated into the garment and is coupled with the flexible material.

15. A system for applying therapeutic stimulation to a human body via a garment with at least one insert disposed thereon, wherein the system comprises:
a garment, wherein the garment comprises:
a flexible material configured to apply compressive forces to a portion of a person wearing the garment;
a thermal element configured to apply heating or cooling to the person;
a thermal port that is integrated into the garment that provides a fluid connection that is configured to provide or remove energy from the thermal element;
a communication interface that is integrated into the garment and that is coupled with the flexible material; and
a first attachment point in a first location; and a first therapeutic insert, wherein:
the first therapeutic insert comprises:
a vibration unit configured to vibrate against the person, and to activate upon a first instruction being received from the communication interface; and
a sensor configured to determine a physiological characteristic of the person; and
the first therapeutic insert is configured to couple with the first attachment point.

16. The system for applying therapeutic stimulation to the human body via the garment with the at least one insert disposed thereon of claim 15, further comprising:
a power and communications port that is integrated into the garment and is coupled with the flexible material, wherein the first therapeutic insert is configured to couple with the power and communications port.

* * * * *